(12) United States Patent
Marchand et al.

(10) Patent No.: US 10,952,625 B2
(45) Date of Patent: Mar. 23, 2021

(54) APPARATUS, METHODS AND COMPUTER PROGRAMS FOR ANALYZING HEARTBEAT SIGNALS

(71) Applicant: WITHINGS, Issy les Moulineaux (FR)

(72) Inventors: Ugo Marchand, Issy les Moulineaux (FR); David Campo, Issy les Moulineaux (FR)

(73) Assignee: WITHINGS, Issy les Moulineaux (FR)

( * ) Notice: Subject to any disclaimer, the term of this patent is extended or adjusted under 35 U.S.C. 154(b) by 141 days.

(21) Appl. No.: 16/212,303

(22) Filed: Dec. 6, 2018

(65) Prior Publication Data
US 2019/0167130 A1    Jun. 6, 2019

(30) Foreign Application Priority Data

Dec. 6, 2017 (EP) .................................... 17205751

(51) Int. Cl.
| | | |
|---|---|---|
| *A61B 5/024* | (2006.01) | |
| *A61B 5/00* | (2006.01) | |
| *A61B 7/04* | (2006.01) | |
| *A61B 5/0255* | (2006.01) | |
| *G16H 50/30* | (2018.01) | |
| *G16H 40/63* | (2018.01) | |
| *G16H 50/20* | (2018.01) | |
| *A61B 5/352* | (2021.01) | |
| *A61B 7/02* | (2006.01) | |

(52) U.S. Cl.
CPC ........ *A61B 5/02438* (2013.01); *A61B 5/0006* (2013.01); *A61B 5/0255* (2013.01); *A61B 5/352* (2021.01); *A61B 5/6824* (2013.01); *A61B 5/7203* (2013.01); *A61B 5/7264* (2013.01); *A61B 7/04* (2013.01); *G16H 40/63* (2018.01); *G16H 50/20* (2018.01); *G16H 50/30* (2018.01); *A61B 7/02* (2013.01)

(58) Field of Classification Search
None
See application file for complete search history.

(56) References Cited

U.S. PATENT DOCUMENTS

| | | | | |
|---|---|---|---|---|
| 2003/0139674 | A1* | 7/2003 | Stergiopoulos | ........ A61B 7/045 600/490 |
| 2004/0092846 | A1* | 5/2004 | Watrous | ................... A61B 7/04 600/586 |
| 2008/0013747 | A1* | 1/2008 | Tran | ..................... A61B 5/0295 381/67 |

(Continued)

OTHER PUBLICATIONS

XP055477879 (https://en.wikipedia.org/wiki/Wavelet).

*Primary Examiner* — Brian T Gedeon
(74) *Attorney, Agent, or Firm* — von Briesen & Roper, s.c.

(57) ABSTRACT

An apparatus, method and computer program, the apparatus comprising: processing circuitry and memory circuitry including computer program code, the memory circuitry and the computer program code arranged to, with the processing circuitry, cause the apparatus to: obtain an audio signal from an audio sensing means wherein the audio signal comprises a subject's heartbeat; obtain a further signal from a further sensing means wherein the further signal also comprises the subject's heartbeat; use the further signal to identify individual heart beats in the audio signal; and analyse the individual heartbeats of the audio signal to enable the audio signal to be classified.

18 Claims, 10 Drawing Sheets

(56) References Cited

U.S. PATENT DOCUMENTS

2011/0257548 A1 10/2011 Dong et al.
2015/0179176 A1* 6/2015 Ryu .................. G06F 3/167
                                         704/275

* cited by examiner

APPARATUS, METHODS AND COMPUTER PROGRAMS FOR ANALYZING HEARTBEAT SIGNALS

CROSS-REFERENCE TO RELATED APPLICATION

This application claims priority under the Paris Convention to European Patent Application No. 17205751.5 filed on Dec. 6, 2017.

FIELD OF THE DISCLOSURE

Examples of the disclosure relate to apparatus, methods and computer programs for analyzing heartbeat signals. In some examples the disclosure relates to apparatus, methods and computer programs for analyzing audio heartbeat signals.

BACKGROUND OF THE DISCLOSURE

Apparatus for obtaining heartbeat signals are known. For example, a stethoscope comprises microphones which can be used to obtain audio signals comprising a subject's heartbeat. Other types of sensors can obtain other types of heartbeat signals. In order to provide useful information to the subject about their heartbeat the heartbeat signals may be analyzed.

SUMMARY OF THE DISCLOSURE

According to various, but not necessarily all, examples of the disclosure there is provided an apparatus comprising: processing circuitry and memory circuitry including computer program code, the memory circuitry and the computer program code arranged to, with the processing circuitry, cause the apparatus to: obtain an audio signal from an audio sensing means wherein the audio signal comprises a subject's heartbeat; obtain a further signal from a further sensing means wherein the further signal also comprises the subject's heartbeat; use the further signal to identify individual heart beats in the audio signal; and analyse the individual heartbeats of the audio signal to enable the audio signal to be classified.

The apparatus, the audio sensing means and the further sensing means may be provided within attachment means for attaching the apparatus to a subject.

The audio sensing means may be positioned within the apparatus so that when the apparatus is attached to the subject the audio sensing means is positioned adjacent to the subject's torso.

The audio sensing means may be positioned within the apparatus so that when the apparatus is attached to a subject the audio sensing means is positioned underneath the subject's arm.

The attachment means may comprise a cuff which is arranged to fit around the subject's arm.

The further sensing means may comprise means for sensing a bioelectric signal.

The bioelectric signal may comprise an electrocardiogram signal.

The memory circuitry and the computer program code may be configured to, with the processing circuitry, cause the apparatus to identify R peaks in the further signal to enable individual heartbeats in the audio signal to be identified.

The memory circuitry and the computer program code may be configured to, with the processing circuitry, cause the apparatus to divide the individual heartbeats of the audio signal into segments corresponding to different portions of the heartbeat.

The memory circuitry and the computer program code may be configured to, with the processing circuitry, cause the apparatus to use wavelets to remove noise from the audio signal.

The memory circuitry and the computer program code may be configured to, with the processing circuitry, cause the apparatus to extract features from within an individual heartbeat of the audio signal and use the extracted features to classify the audio signal.

According to various, but not necessarily all, examples of the disclosure there is provided an apparatus comprising: processing circuitry and memory circuitry including computer program code, the memory circuitry and the computer program code arranged to, with the processing circuitry, cause the apparatus to: obtain an audio signal from one or more audio sensors wherein the audio signal comprises a subject's heartbeat; obtain a further signal from one or more further sensors wherein the further signal also comprises the subject's heartbeat; use the further signal to identify individual heart beats in the audio signal; and analyse the individual heartbeats of the audio signal to enable the audio signal to be classified.

The apparatus, the one or more audio sensors and the one or more further sensors may be provided within an attachment portion for attaching the apparatus to a subject.

The apparatus may comprise a user interface enabling a user to interact with the apparatus, and enabling the apparatus to provide a feedback to the user.

The user interface may comprise a display arranged to output information for the user.

The user interface may comprise a loudspeaker arranged to output information for the user.

According to various, but not necessarily all, examples of the disclosure there may be provided a wearable device comprising an apparatus as described above.

According to various, but not necessarily all, examples of the disclosure there may be provided a method comprising:
S1- obtaining an audio signal from an audio sensing means wherein the audio signal comprises a subject's heartbeat;
S2- giving a feedback to the user upon determination that the obtained audio signal has a quality level below a given threshold, and in which case causing step S1 to be repeated,
S3- obtaining a further signal from a further sensing means wherein the further signal also comprises the subject's heartbeat;
S4- giving a feedback to the user upon determination that the obtained further signal has a quality level below a given threshold, and in which case causing step S3 to be repeated,
S5- using the further signal to identify individual heart beats in the audio signal; and
S6- analysing the individual heartbeats of the audio signal,
S7- classifying the individual heartbeats,
S8- providing a result to the user as to whether the heartbeat of the subject is normal or abnormal.

According to one possible feature, the method may include an initial step of:
S0- initiating the auscultation sequence. This initial step (starting step) can be done via a start cycle pushbutton, an ON/OFF pushbutton or a voice control.

According to one option, the method may comprise after step S1 a noise removing process using a wavelet signal transform (convolution or similar process) to retain significant signal portions and to remove noise from the audio signal.

According to one option, the method may comprise after step S3 a noise removing process using a wavelet signal (convolution or similar process) to retain significant signal portions and to remove noise from the further signal.

According to one option, during step S2 when a quality level of the audio signal is be determined, the method may include the determination of a speech occurrence, either a subject speech of other people talk around nearby.

According to one option, the determination of a speech occurrence is made via assessment of zero-crossing rate and spectral flatness on one or more portions of the audio signal.

According to one option, the method may further comprise:
S9- forwarding the recorded audio signal, named a phonocardiogram, from the apparatus to a remote device having a loudspeaker therein,
S10- replaying on demand, at the remote device, said phonocardiogram via the loudspeaker.

According to various, but not necessarily all, examples of the disclosure there may be provided a computer program comprising computer program instructions that, when executed by processing circuitry, cause: obtaining an audio signal from an audio sensing means wherein the audio signal comprises a subject's heartbeat; obtaining a further signal from a further sensing means wherein the further signal also comprises the subject's heartbeat; using the further signal to identify individual heartbeats in the audio signal; and analysing the individual heartbeats of the audio signal to enable the audio signal to be classified.

According to various, but not necessarily all, examples of the disclosure there is provided examples as claimed in the appended claims.

BRIEF DESCRIPTION OF THE DRAWINGS

For a better understanding of various examples that are useful for understanding the detailed description, reference will now be made by way of example only to the accompanying drawings in which.

DETAILED DESCRIPTION OF THE DISCLOSURE

Examples of the disclosure relate to an apparatus 1, method and computer program for analysing heartbeat signals from a subject 31. The apparatus 1 can be operated by an unskilled user, who may be the subject 31, so that the heartbeat signals can be obtained and analysed at any convenient time.

The apparatus 1 can be operated at home, without the presence of a physician or doctor. The apparatus 1 can be operated by the subject himself/herself, in a self-auscultation configuration.

Also, the apparatus 1 can be operated by a helping person other than the subject. The helping person can be a caregiver or a relative.

Figure 1:
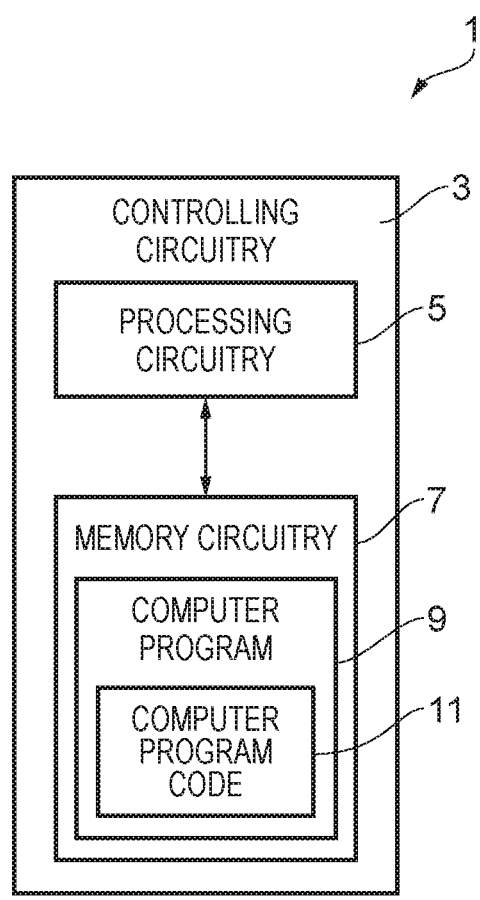
FIG. 1 illustrates an apparatus.

FIG. 1 schematically illustrates an apparatus 1 according to examples of the disclosure. The apparatus 1 illustrated in FIG. 1 may be a chip or a chip-set. In some examples the apparatus 1 may be provided within devices such as a sensing device or a processing device or any other suitable device. In some examples the apparatus 1 may be provided within a wearable device that can be attached to the body of a subject 31.

The apparatus 1 comprises controlling circuitry 3. The controlling circuitry 3 may provide means for controlling an electronic device such as a sensing device or a processing device. The controlling circuitry 3 may also provide means for performing the methods, or at least part of the methods, of examples of the disclosure.

The apparatus 1 comprises processing circuitry 5 and memory circuitry 7. The processing circuitry 5 may be configured to read from and write to the memory circuitry 7. The processing circuitry 5 may comprise one or more processors. The processing circuitry 5 may also comprise an output interface via which data and/or commands are output by the processing circuitry 5 and an input interface via which data and/or commands are input to the processing circuitry 5.

The memory circuitry 7 may be configured to store a computer program 9 comprising computer program instructions (computer program code 11) that controls the operation of the apparatus 1 when loaded into processing circuitry 5. The computer program instructions, of the computer program 9, provide the logic and routines that enable the apparatus 1 to perform the example methods described. The processing circuitry 5, by reading the memory circuitry 7, is able to load and execute the computer program 9.

The computer program 9 may arrive at the apparatus 1 via any suitable delivery mechanism. The delivery mechanism may be, for example, a non-transitory computer-readable storage medium, a computer program product, a memory device, a record medium such as a compact disc read-only memory (CD-ROM) or digital versatile disc (DVD), or an article of manufacture that tangibly embodies the computer program. The delivery mechanism may be a signal configured to reliably transfer the computer program 9. The apparatus 1 may propagate or transmit the computer program 9 as a computer data signal. In some examples the computer program code 9 may be transmitted to the apparatus 1 using a wireless protocol such as Bluetooth, Bluetooth Low Energy, Bluetooth Smart, 6LoWPan (IP$_v$6 over low power personal area networks) ZigBee, ANT$_+$, near field communication (NFC), Radio frequency identification, wireless local area network (wireless LAN) or any other suitable protocol.

Although the memory circuitry 7 is illustrated as a single component in the figures it is to be appreciated that it may be implemented as one or more separate components some or all of which may be integrated/removable and/or may provide permanent/semi-permanent/dynamic/cached storage.

Although the processing circuitry 5 is illustrated as a single component in the figures it is to be appreciated that it may be implemented as one or more separate components some or all of which may be integrated/removable.

References to "computer-readable storage medium", "computer program product", "tangibly embodied computer program" etc. or a "controller", "computer", "processor" etc. should be understood to encompass not only computers having different architectures such as single/multi-processor architectures, Reduced Instruction Set Computing (RISC) and sequential (Von Neumann)/parallel architectures but also specialized circuits such as field-programmable gate arrays (FPGA), application-specific integrated circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term "circuitry" refers to all of the following:
(a) hardware-only circuit implementations (such as implementations in only analog and/or digital circuitry) and
(b) to combinations of circuits and software (and/or firmware), such as (as applicable): (i) to a combination of processor(s) or (ii) to portions of processor(s)/software (including digital signal processor(s)), software, and memory(ies) that work together to cause an apparatus, such as a mobile phone or server, to perform various functions) and
(c) to circuits, such as a microprocessor(s) or a portion of a microprocessor(s), that require software or firmware for operation, even if the software or firmware is not physically present.

This definition of "circuitry" applies to all uses of this term in this application, including in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile phone or a similar integrated circuit in a server, a cellular network device, or other network device.

Figure 2:
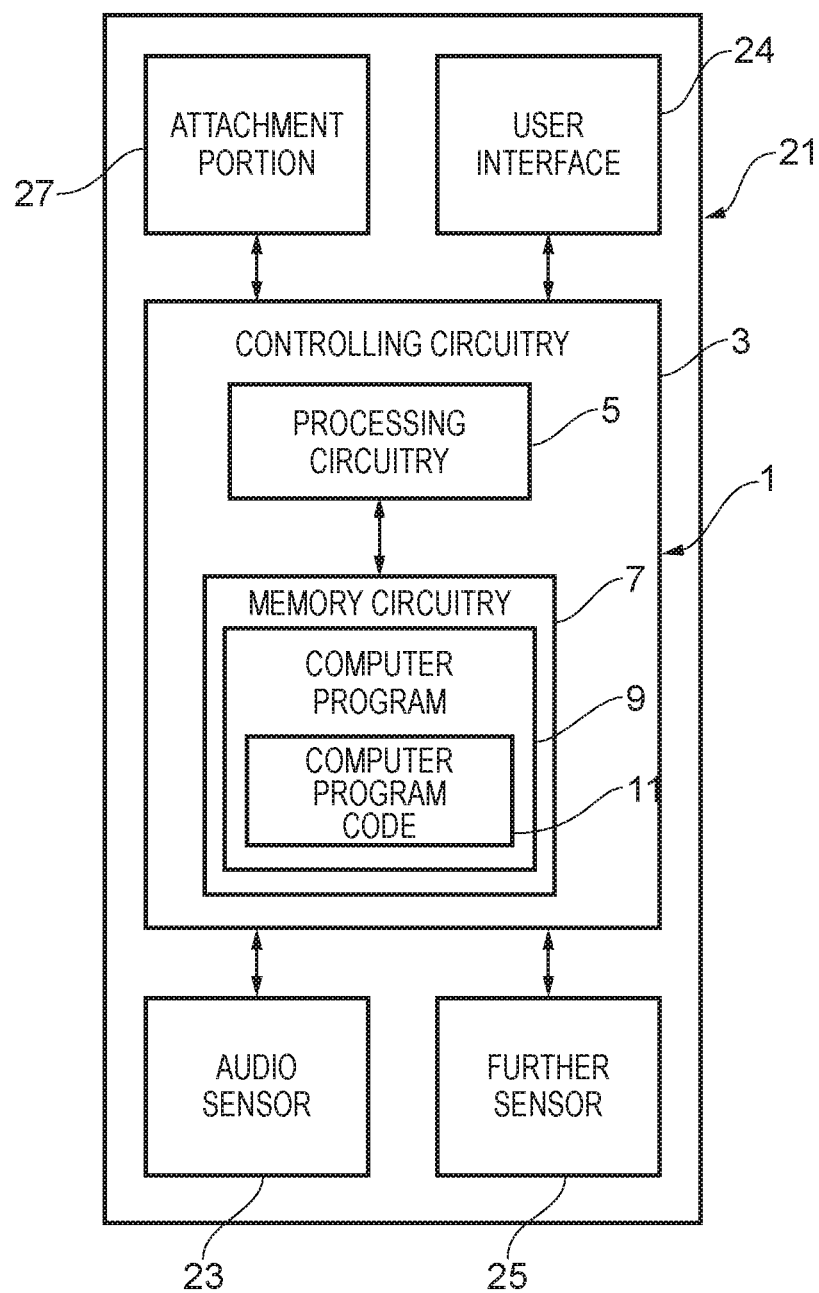
FIG. 2 illustrates a wearable device comprising an apparatus.

FIG. 2 schematically illustrates a wearable device 21 comprising an apparatus 1. The apparatus 1 may comprise controlling circuitry 3 described above. Corresponding reference numerals are used for corresponding features.

The example wearable device 21 also comprises one or more audio sensors 23, one or more further sensors 25, an attachment portion 27 and a user interface 29. It is to be appreciated that the wearable device 21 may also comprise other components that are not illustrated in FIG. 2. For example, the wearable device 21 may comprise a power source and any other suitable components.

The audio sensors 23 provide audio sensing means. The audio sensors 23 may comprise any means for detecting a sound signal and transducing the sound signal into an electrical output signal. The audio sensors 23 may comprise one or more microphones.

In some examples the wearable device 21 might comprise a single audio sensor 23. In other examples more than one audio sensor 23 could be provided within the wearable device 21.

The sound signal that is detected by the audio sensor 23 may comprise a subject's heartbeat. The audio sensors 23 may be positioned within the wearable device 21 so that when the wearable device 21 is worn by a subject 31 the audio sensor 23 is positioned adjacent to the subject's torso. This positioning may enable the audio sensor 23 to detect the sound signal comprising the heartbeat. The electrical output signal provided by the audio sensors 23 may therefore be an audio signal comprising a heartbeat.

The audio sensors 23 may be coupled to the controlling circuitry 3. This may enable the controlling circuitry 3 to be used to control the audio sensors 23. The audio sensors 23 may also be arranged to provide the audio signal comprising a heartbeat to the controlling circuitry 3. This enables the audio signal comprising a heartbeat to be analysed by the controlling circuitry 3.

The further sensors 25 provide further sensing means. The further sensors 25 may comprise any means for detecting a signal comprising the subject's heartbeat and providing an electrical output signal indicative of the heartbeat. The electrical output signal provided by the further sensors 25 may therefore be a further signal comprising a heartbeat.

The signal that is detected by the further sensors 25 could be a different type of heartbeat signal to the sound signals detected by the audio sensors 23. For example the further sensors 25 could be arranged to detect a bioelectric signal such as an ECG (electrocardiogram) signal or any other suitable type of heartbeat signal. The further sensors 25 may comprise one or more electrodes arranged to detect the ECG signal or other type of heartbeat signal.

The further sensors 25 are positioned within the wearable device 21 so that when the wearable device is being worn by a subject 31 the further sensors 25 can be positioned adjacent to part of the subject's body. This positioning may enable the further sensor 25 to detect the heartbeat signals.

The further sensors 25 may be positioned at a different location within the wearable device to the audio sensors 23. This may enable the further sensors 25 and the audio sensors 23 to detect the heartbeat signals from different parts of the subject's body.

The further sensors 25 may be coupled to the controlling circuitry 3. This may enable the controlling circuitry 3 to be used to control the further sensors 25. The further sensors 25 may also be arranged to provide the further signal comprising a heartbeat to the controlling circuitry 3. This enables the further signal comprising a heartbeat to be analysed by the controlling circuitry 3.

The attachment portion 27 is shown schematically in FIG. 2. The attachment portion 27 may comprise any attachment means for enabling the wearable device 21 to be attached to the body of a subject 31. In some examples the wearable portion 27 may comprise a cuff or a sleeve that is arranged to be worn around the subject's arm. Other types of attachment portion 27 may be used in other examples.

The components of the wearable device 21 are coupled to the attachment portion 27 so that when the attachment portion 27 is attached to a subject 31 the audio sensors 23 and the further sensors 25 can detect the heartbeat signals from the subject 31. In some examples components of the wearable device 21 may be provided within the attachment portion 27. For instance, the audio sensors 23, the further sensors 25, the user interface 29 and the apparatus 1 may all be provided within a cuff or sleeve.

In some examples of the disclosure the wearable device 21 may also comprise a user interface 29. The user interface 29 may comprise means for enabling a subject 31 to interact with the wearable device 21. The user interface 29 may comprise means for providing information to the subject 31. For example the user interface 29 could comprise a display or a loudspeaker that could be arranged to output information for the subject 31. The information provided by the user interface 29 could comprise information relating to the detected heartbeat signals, the operation of the wearable device 21 or any other suitable information.

The user interface 29 may be coupled to the controlling circuitry 3 so that the user interface 29 can be controlled by the controlling circuitry 3. This may also enable user inputs to be provided to the controlling circuitry 3 to enable a user to control the operation of the wearable device 21.

It is to be appreciated that in some examples there may be more than one wearable device 21. For example, some features of the wearable device 21 as described herein may be arranged across a plurality of wearable devices 21 in any suitable configuration, where the plurality of wearable devices 21 are configured to be operated together. As one example, a first wearable device 21 may comprise audio sensors 23 and no further sensors 25, whereas a second wearable device 21 may comprise further sensors 25 and no audio sensors 23, and so on. For convenience, the rest of this description refers to the example where only one wearable device 21 is used.

There may be provided in the apparatus an ON/OFF pushbutton for switching on the device, and/or for starting an auscultation cycle. Voice control is not excluded as an alternative solution.

Figure 3:
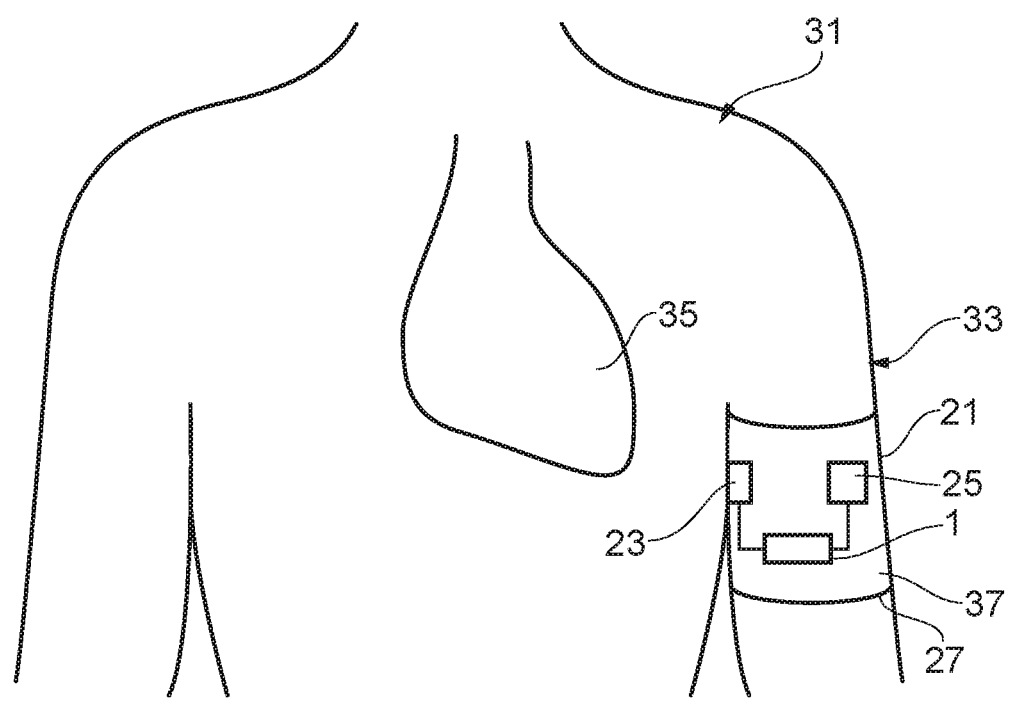
FIG. 3 illustrates a subject using a wearable device.

FIG. 3 illustrates a subject 31 using a wearable device 21. The wearable device could be a wearable device 21 as shown in FIG. 2. The wearable device 21 comprises an audio sensor 23, a further sensor 25 and an apparatus 1 coupled to the sensors 23, 25. The wearable device 21 may also comprise a user interface 29 which is not shown in FIG. 3. In the example of FIG. 3 the subject 31 is a person. In other examples the subject 31 could be an animal.

In the example of FIG. 3 the attachment portion 27 has been used to attach the wearable device 21 to the body of the subject 31. FIG. 3 shows the wearable device 21 attached to the arm 33 of the subject 31. The wearable device 21 has been attached to the upper arm 33 of the subject 31. The attachment portion 27 may comprise a cuff 37 which may be sized and shaped to fit around the arm 33 of the subject 31. The cuff 37 may be adjustable to ensure that it fits tightly around the arm 33 of the subject 31. It is to be appreciated that the wearable device 21 could be coupled to other parts of the subject's body in other examples of the disclosure.

The audio sensor 23 is provided on an outer surface, or close to an outer surface, of the cuff 37. This enables the audio sensor 23 to be positioned in close proximity to the body of the subject 31 so that the audio sensor 23 can detect sound signals from the body of the subject 31. The cuff 37 can be positioned, as shown in FIG. 3, so that the audio sensor 23 is positioned adjacent to the torso of the subject 31. In this example the audio sensor 23 may be positioned underneath the arm 33 of the subject 31. This enables the audio sensor 23 to detect sound signals generated by the subject's heart 35. The audio sensor 23 could be located in different locations in other implementations of the disclosure.

The further sensor 25 may also be positioned on an outer surface, or close to an outer surface, of the cuff 37. The further sensor 25 may be positioned on the outer surface, or close to the outer surface, of the cuff 37 so that the subject 31 can cover the further sensor 25 with the hand from the opposite arm to the one wearing the cuff 37. In some examples two or more further sensors 25 may be provided.

For example, a first further sensor 25 may be provided on an inner surface of the cuff 37 and a second further sensor 25 may be provided on an outer surface of the cuff 37. This may enable a heartbeat signal, such as an ECG signal, which requires at least two electrodes positioned at different locations, to be detected through the further sensors 25. Other positions and types of further sensor 25 may be used in other examples of the disclosure. The position and type of further sensor 25 that is used may depend upon the type of further signal that is to be detected by the further sensor 25.

The apparatus 1 is provided within the wearable device 21 and may be coupled to the audio sensor 23 and the further sensor 25 so that the apparatus 1 obtains the audio signal and the further signal from the sensors 23, 25. The controlling circuitry 3 within the apparatus 1 may be arranged to analyse the audio signals and the further signals. The analysis of the audio signal and the further signal may enable the audio signals to be classified. This classification may provide an indication as to whether the subject 31 is healthy or unhealthy or any other suitable information. Example methods for analyzing the heartbeat signals are shown in FIGS. 4 and 5.

Figure 4:
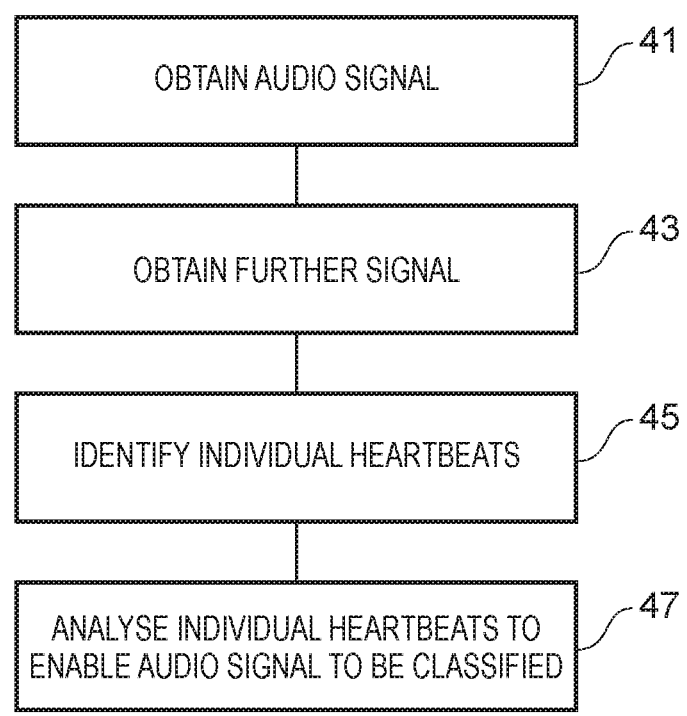
FIG. 4 illustrates a method.
Figure 5:
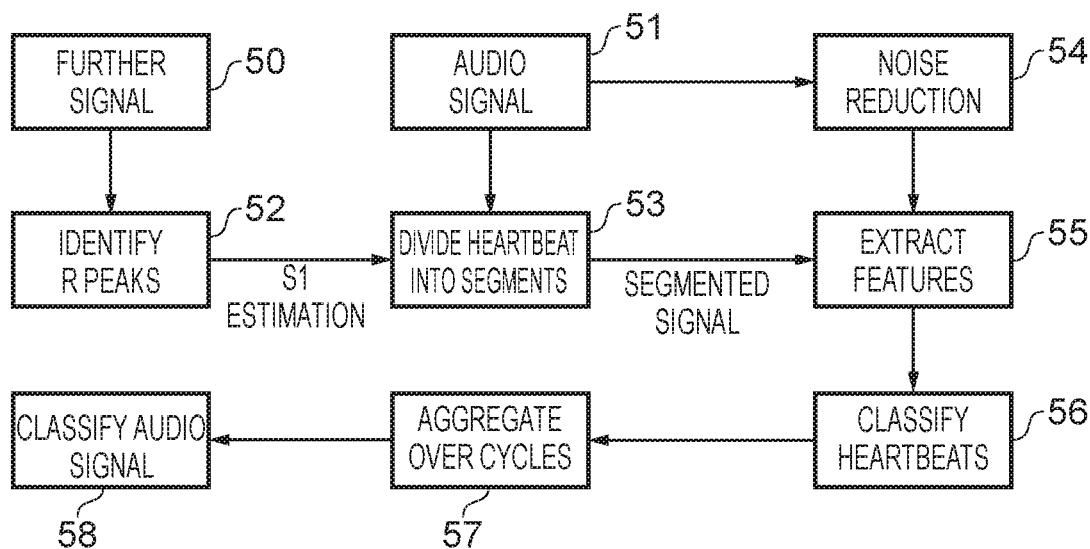
FIG. 5 illustrates a method.

FIG. 4 illustrates an example method for analyzing heartbeat signals. The heartbeat signals may comprise any signals that comprise a subject's heartbeat. The method of FIG. 4 may be implemented using apparatus 1 and a wearable device 21 as described above.

The method comprises, at block 41, obtaining an audio signal. The apparatus 1 may obtain the audio signal from an audio sensor 23. The audio signal comprises a subject's heartbeat.

The method also comprises at block 43 obtaining a further signal. The apparatus 1 may obtain the further signal from a further sensor 25. The further signal also comprises the subject's heartbeat. The further sensor 25 may detect the subject's heartbeat using a different type of signal to a sound signal.

At block 45 the method comprises using the further signal to identify individual heartbeats in the audio signal. The further signal may be used to identify features that are present in every heartbeat. The further signal may identify the features more reliably than they can be identified using the audio signal alone.

At block 47 the method comprises analysing the individual heartbeats of the audio signal to enable the audio signal to be classified. An output indicative of the classification of the audio signal may be provided via the user interface 29.

FIG. 5 illustrates an example method for analyzing heartbeat signals in further detail. FIGS. 6 to 11 show further details of the blocks in the method of FIG. 5. The method of FIG. 5 may be implemented using apparatus 1 and a wearable device 21 as described above.

At block 50 the further signal is obtained by the apparatus 1. The further signal may be obtained from one or more further sensors 25. The further signal may comprise an electrical output signal from the further sensors 25 where the electrical output signal comprises the subject's heartbeat.

The further signal may comprise a signal in which features of the subject's heartbeat are clear enough to enable individual heartbeats to be identified. In the example of FIG. 5 the further signal comprises an ECG signal. In other examples other types of further signal could be used instead of, or in addition to, the ECG signal.

Figure 6:
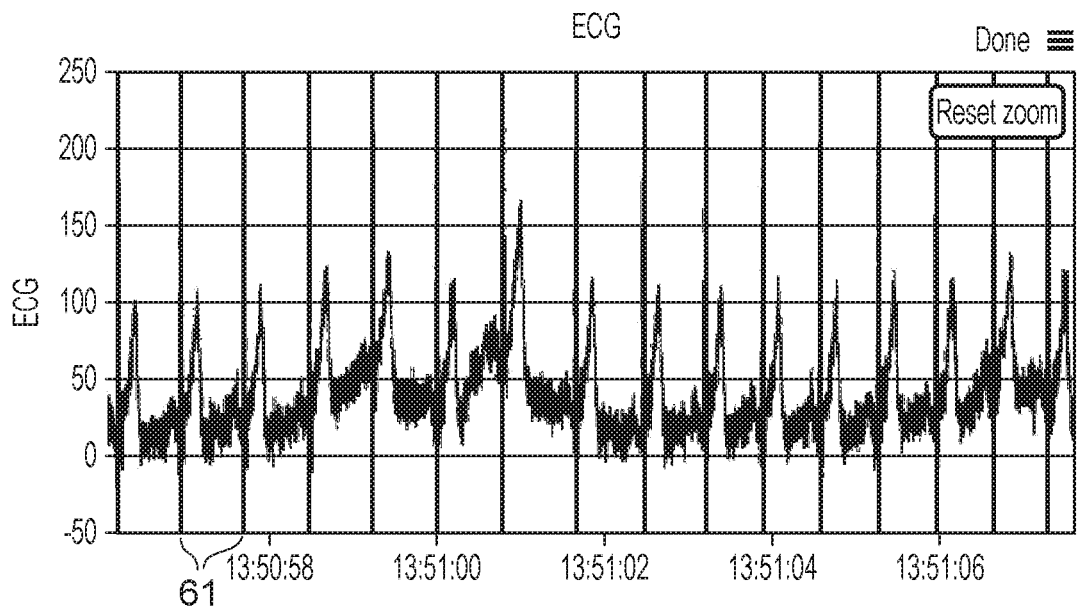
FIG. 6 illustrates an identification of heartbeats in a signal.

At block 52 the further signal is used to identify individual heart beats within the further signal. In the example of FIG. 5 the further signals comprises an ECG signal and at block 52 the R peaks within the ECG signal are identified. FIG. 6 shows an example of identified R peaks 61 in an ECG signal.

The R peaks 61 can be used as an estimation of the S1 phase of the heartbeat. That is, the R peaks 61 enable a particular phase of the heartbeat to be identified. This provides more detailed information than detecting just the pulse of the subject 31.

The estimation of the S1 phase of the heartbeat provides an indication of the start of each heartbeat. This can therefore enable individual heartbeats to be identified in the further signal and also the audio signal. It is to be appreciated that other peaks or features within a heartbeat signal may be used in other examples of the disclosure.

The R peaks 61 may be identified using an algorithm or any other suitable process.

At block 51 the audio signal is obtained by the apparatus 1. The audio signal may be obtained from one or more audio sensors 23. The audio signal may comprise an electrical output signal from the audio sensors 23 where the electrical output signal comprises the subject's heartbeat.

The further sensor 25 and the audio sensors 23 may detect the heartbeat signals simultaneously. This may enable the identification of the individual heartbeats in the further signal to be used to identify the individual heartbeats in the audio signal.

At block 53 the individual heartbeats of the audio signal are divided into segments corresponding to different portions of the heartbeat. The estimations of the locations of the S1 phase obtained from the further signal can be used to identify the individual heart beats and enable the segmentation of the individual heartbeats.

In order to divide the individual heartbeat into segments a sub-signal corresponding to the signal between two consecutive R peaks 61, as identified at block 52, may be taken. The sub-signal can then be analysed to identify features within the sub-signals. The features may correspond to different phases of the heartbeat and may enable the different segments of the heartbeats to be identified.

Figure 7A:
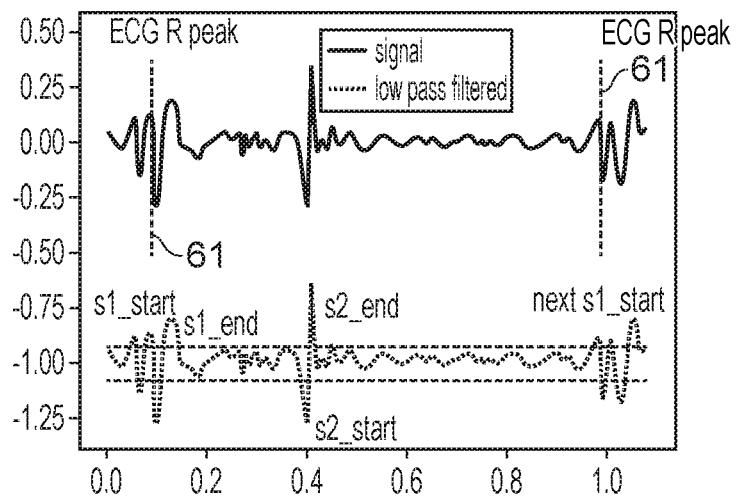
FIGS. 7A to 7C illustrate segmentation of heartbeats.
Figure 7B:
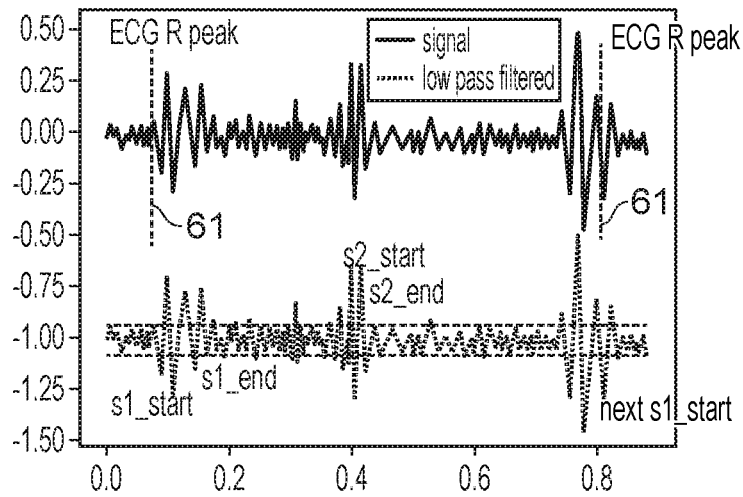
Figure 7C:
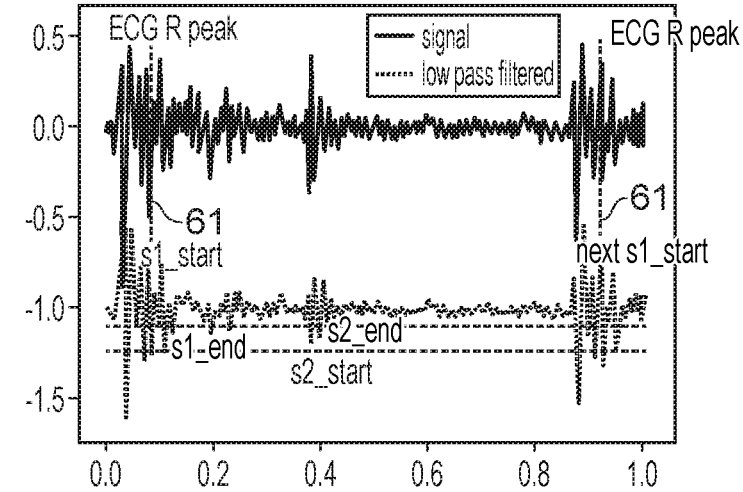

FIGS. 7A to 7C show examples of different segments of a heartbeat that may be used in some examples of the disclosure. FIG. 7A shows the audio signals obtained for a healthy subject 31, FIG. 7B shows the audio signals obtained for a subject 31 with aortic stenosis and FIG. 7C shows the audio signals obtained for a subject 31 with mitral regurgitation. In each of FIGS. 7A to 7C the upper trace shows the obtained raw audio signal and the lower trace shows the filtered audio signal.

The audio signals are divided into individual heartbeats by identifying the R peaks 61 from the ECG signal. The R peaks 61 are indicated by the dashed lines in FIGS. 7A to 7C. The R-peaks 61 provides an indication of the start of the S1 phase of the heartbeat.

The shape of the sub-signal between two adjacent R-peaks 61 can then be analysed to identify key features within the sub-signal. The identified features may correspond to phases of the heartbeat. In the example of FIGS. 7A to 7C the key features identifies are the start of the S1 segment, the end of the S1 segment, the start of the S2 segment, the end of the S2 segment and the start of the next S1 segment. These features can be identified in both healthy subjects and subjects with heart conditions. This enables the same segmentation to be accurate for both healthy and unhealthy subjects.

Figure 8:
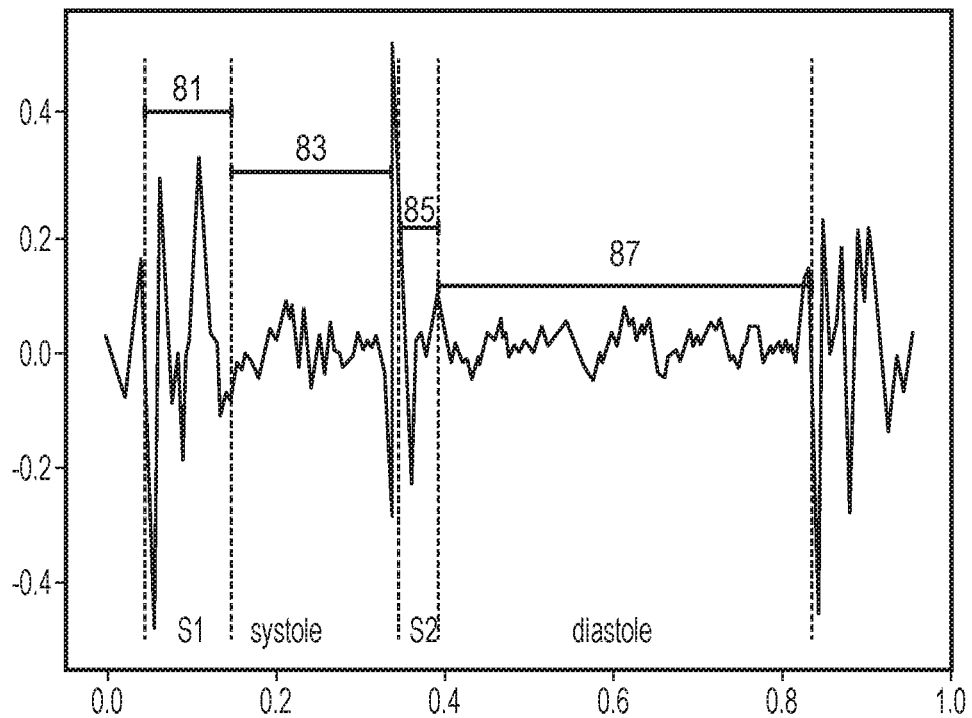
FIG. 8 illustrates segmentation of a heartbeat.

FIG. 8 illustrates an example of the segments of the individual heartbeat. In this example the heartbeat is divided into four consecutive segments. Other numbers of segments could be used in other examples of the disclosure. In the example of FIG. 8 the first segment 81 comprises the S1 phase, the second segment 83 comprises the systole phase, the third segment 85 comprises the S2 phase and fourth segment 87 comprises the diastole phase. These segments 81, 83, 85, 87 cover different phases of the heartbeat and may each have distinctive features which enable the heartbeats to be classified.

In the example of FIG. 8 the different segments 81, 83, 85, 87 have different lengths of time. For example the fourth segment 87 which covers the diastole phase covers a longer time period than any of the other segments 81, 83, 85. The third segment 85 which covers the S2 phase covers a shorter time period than any of the other segments 81, 83, 87.

It is to be appreciated that different ways of dividing the heartbeat into different segments could be used in other examples of the disclosure. In the example of FIGS. 7A to 7C and 8 the segments 81, 83, 85, 87 run sequentially from each other so that when one segment finishes the next segment begins. In other examples there may be some overlap between one or more of the segments so that some two or more segments may comprise the same information.

The algorithm used to identify the key features and divide the heartbeat into segments 81, 83, 85, 87 could be a state machine with heuristic hard coded rules. Other types of processes and algorithms could be used in other examples. For instance, in some cases a machine learning algorithm could be used.

At block 54 in FIG. 5, the noise within the audio signal is reduced. The noise reduction may suppress noise from unwanted sound sources. For example, the noise reduction may act to remove and/or reduce noise from sources such as the lungs of the subject 31, speech of the subject 31, background noise or any other unwanted source of noise, in particular people talk.

Figure 9A:
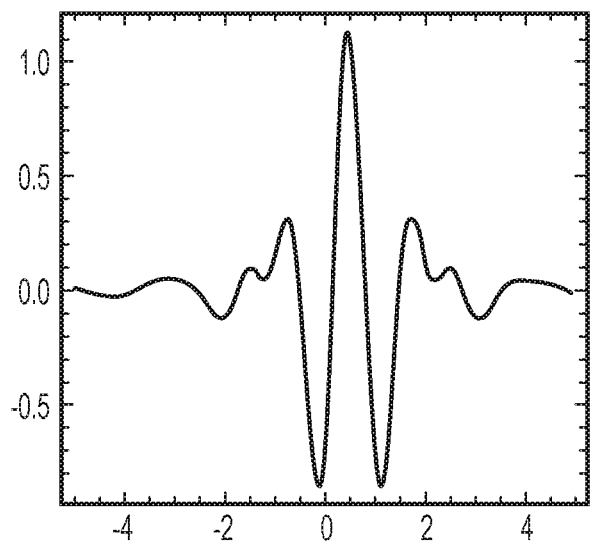
FIGS. 9A and 9B illustrate wavelets that may be used for noise reduction.
Figure 9B:
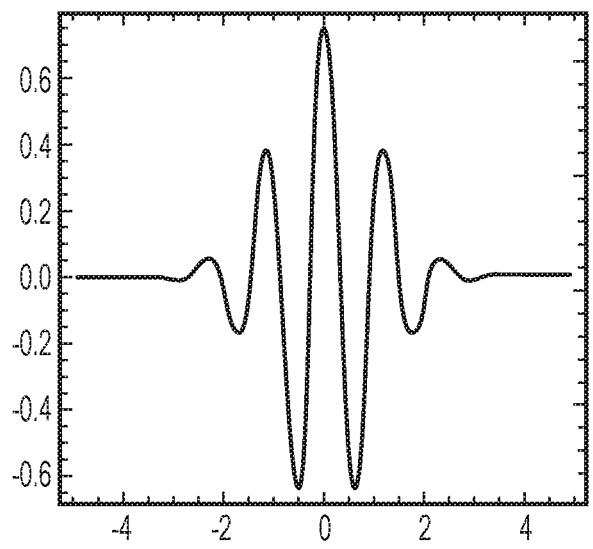

In some examples wavelet de-noising may be used to remove or reduce the noise in the audio signal. The wavelets used may be selected to have a similar shape to the shape of the heartbeat within the heartbeat signal. FIGS. 9A and 9B show example wavelets that may be used to reduce noise within the audio signal. FIG. 9A illustrates a Meyer wavelet and FIG. 9B illustrates a Morlet Wavelet. Other types of wavelets may be used in other examples of the disclosure.

The wavelet noise reduction process may comprise transforming the raw audio signal from the time domain to a different domain. In some examples a Fourier transform, or other suitable transform, could be used to transform the raw audio signal into the frequency domain. The wavelets can then be used to remove low coefficients and the signal can then be transformed back into the time domain.

Figure 10A:
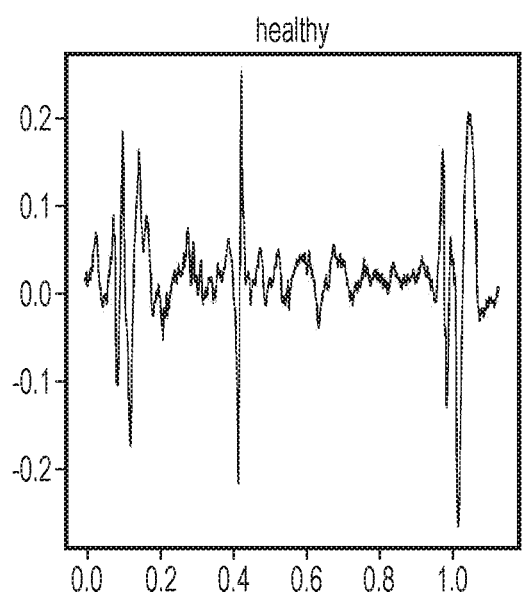
FIGS. 10A to 10F illustrate noise reduction of heartbeat signals.
Figure 10B:
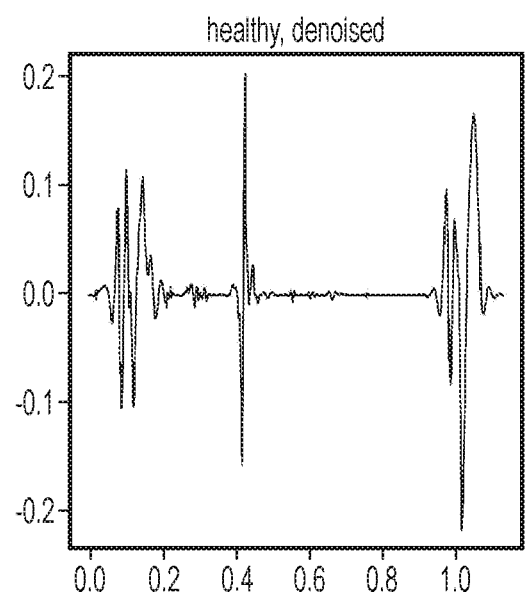
Figure 10C:
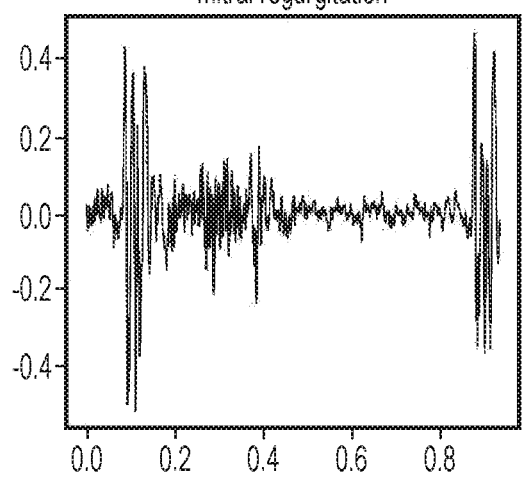
Figure 10D:
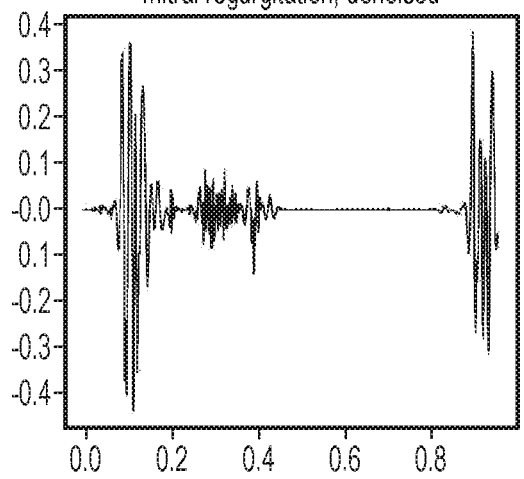
Figure 10E:
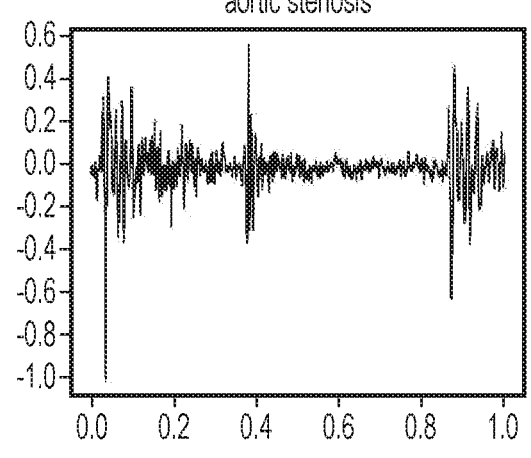
Figure 10F:
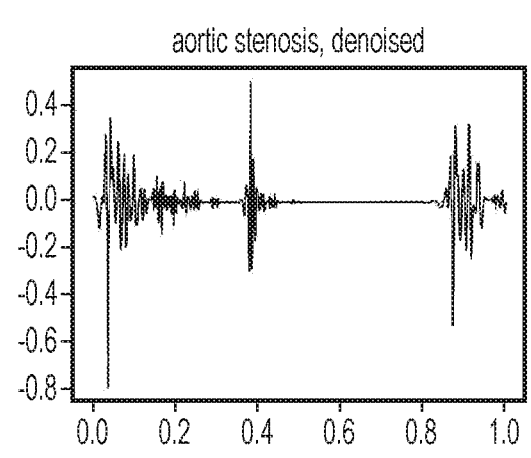

FIGS. 10A to 10F show examples of noise reduction using wavelets in audio signals. FIG. 10A shows a raw audio signal from a healthy subject 31 and FIG. 10B shows the signal from the healthy subject 31 after the noise has been removed. FIG. 10C shows a raw audio signal from a subject 31 with mitral regurgitation and FIG. 10D shows the signal from the subject 31 with mitral regurgitation after the noise has been removed. FIG. 10E shows a raw audio signal from a subject 31 with aortic stenosis and FIG. 10F shows the signal from the subject 31 with aortic stenosis after the noise has been removed. It can be seen from FIGS. 10A to 10F that the wavelet noise reduction works well with both signals from a healthy subject 31 and also a subject 31 that has a heart condition. This enables the methods to be used both with healthy subjects 31 and subjects 31 with heart conditions.

A noise removing process (de-noising) using wavelets on a signal of interest relies on a wavelet transform (convolution or similar process) to retain significant signal portions, in function of scaling factor and time shift coefficients. The wavelet transform enables to remove noise from the signal of interest, directly by obtaining the significant signal portions or by subtracting undesired noisy signal from the raw signal of interest.

In some examples the noise reduction may be carried out at the same time as the dividing of the heartbeat into segments. In other examples the noise reduction may be carried out before the dividing of the heartbeat into segments 81, 83, 85, 87. This may enable the reduced noise signal to be divided into the respective segments 81, 83, 85, 87.

Figures 11, 12:
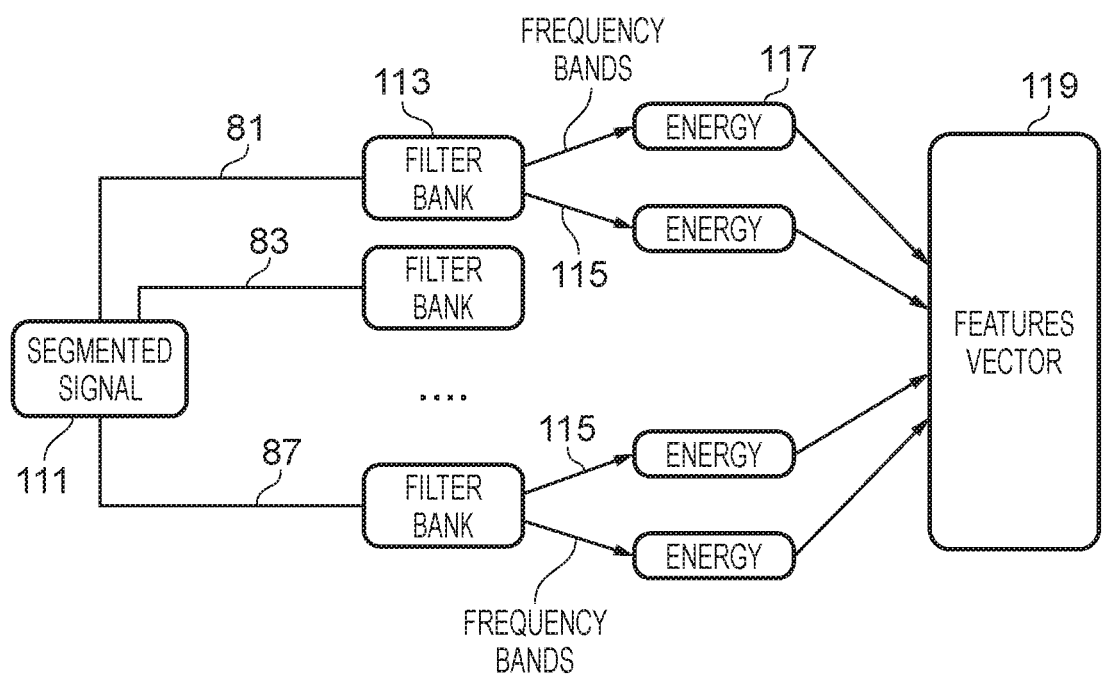
FIG. 11 illustrates a method of extracting features from an audio signal.
FIG. 12 illustrates an example classifier.

At block 55 of the method in FIG. 5 the apparatus 1 extracts features from the audio signal. In the example of FIG. 5 the apparatus 1 extracts the features from the reduced noise signal. FIG. 11 illustrates a method of extracting features that may be performed at block 55.

The example method of FIG. 11 is performed on the segmented audio signal. At block 111 the segmented audio signal is obtained. At block 113 different segments 81, 83, 85, 87 of the audio signal are provided to different filter banks. In the example method of FIG. 11 only three of the segments are shown for clarity, however it is to be appreciated that all of the segments may be provided to the filter banks.

In the example method of FIG. 11 a separate filter bank is provided for each segment 81, 83, 85, 87 so that each segment 81, 83, 85, 87 may be provided to a different filter bank. In the example method of FIG. 11 each of the filter banks are the same.

That is, each of the filter banks are arranged to remove the same frequencies so that the same filtering is applied to each segment 81, 83, 85, 87 of the heartbeat. In other examples of the disclosure different filters could be used for the different segments 81, 83, 85, 87 so that different frequencies are removed from the signal for the different segments 81, 83, 85, 87. This may enable the filters used to be optimised for the different segments 81, 83, 85, 87.

At block 115 the filtered segments are divided into frequency bands. In the example of FIG. 11 each segment 81, 83, 85, 87 is divided into seven frequency bands. Other numbers of frequency bands may be used in other examples of the disclosure.

In some examples different sized frequency bands may be used for different parts of a frequency spectrum within each segment 81, 83, 85, 87. The sizes of the frequency bands may be determined using a psychoacoustic scale. In some examples the frequency bands that are used for low frequencies may be narrower than the frequency bands for high frequencies. The sizes of the frequency bands used may be selected to compensate for human hearing.

At block 117 the energy in each of the different frequency bands is determined. Block 117 is performed for each of the frequency bands for each of the segments 81, 83, 85, 87 within the heartbeat. The energies of each of the different frequency bands for each of the segments 81, 83, 85, 87 are then combined, at block 119, to give a features vector. The components of the features vector correspond to the different energy levels in the different frequency bands in each of the segments 81, 83, 85, 87 of the heartbeat. The features vector can be used to identify the features within the heartbeat. The segmentation of the heartbeat enables different features within the different segments to be identified.

Other methods could be used at block 55 of the method of FIG. 5.

Once the features have been identified the method, of FIG. 5 comprises, at block 56, classifying the heartbeat. The classification may comprise using the identified features to group the heartbeat into a class. The different classes may represent different physical conditions of the subject 31 and the heart 35 of the subject 31.

FIG. 12 shows an example error matrix for a system that may be used to classify the heartbeat. In the example of FIG. 12 a random forest classifier is used. Other types of classifier may be used in other examples of the disclosure. The classifier that is used may have a low computational requirement to ensure that the classification can be performed by the processing circuitry 5 within the apparatus 1 of the wearable device 21.

The example of FIG. 12 shows that the random forest classifier gives a predicted probability of whether or not an audio signal belongs to class 1 or class 2. This classifier can therefore be used to distinguish between class 1 and class 2 for the audio signals. Class 1 may represent healthy subjects 31 with no heart condition. Class 2 may represent unhealthy subjects 31 with a heart condition.

In the example of FIG. 12 the classifier can distinguish between healthy and unhealthy audio signals. In some examples more than two classes might be available. This may enable the method to be used, not just to distinguish between healthy and unhealthy signals, but to distinguish between different types of heart conditions.

Once an individual heartbeat has been classified the process of blocks 50 to 56 may be repeated for another heartbeat. This enables the classification to be aggregated over a plurality of cycles. The process may be repeated on the same subject 31 and/or on different subjects 31. The classifications of the heartbeat signals may be aggregated over a plurality of cycles at block 57 in the method of FIG. 5.

At block 58 the aggregated heartbeat cycles may be used to classify the audio signal. The audio signal can be classified in class 1 or class 2 as determined by the outcome of the aggregation. This may enable a subject to be identified as healthy or unhealthy based on the features within the different segments of the heartbeat. This classification could be used to assist in the diagnosis of a medical condition. For example, if the classification shows that the subject 31 is unhealthy it may prompt a physician to carry out further tests.

An output indicative of the classification may be provided by the user interface 29. The output could be an audio or visual output. The output may provide an indication of the class in which the audio signal has been classified. In some examples the output may provide further instructions for the subject 31.

Figure 13:
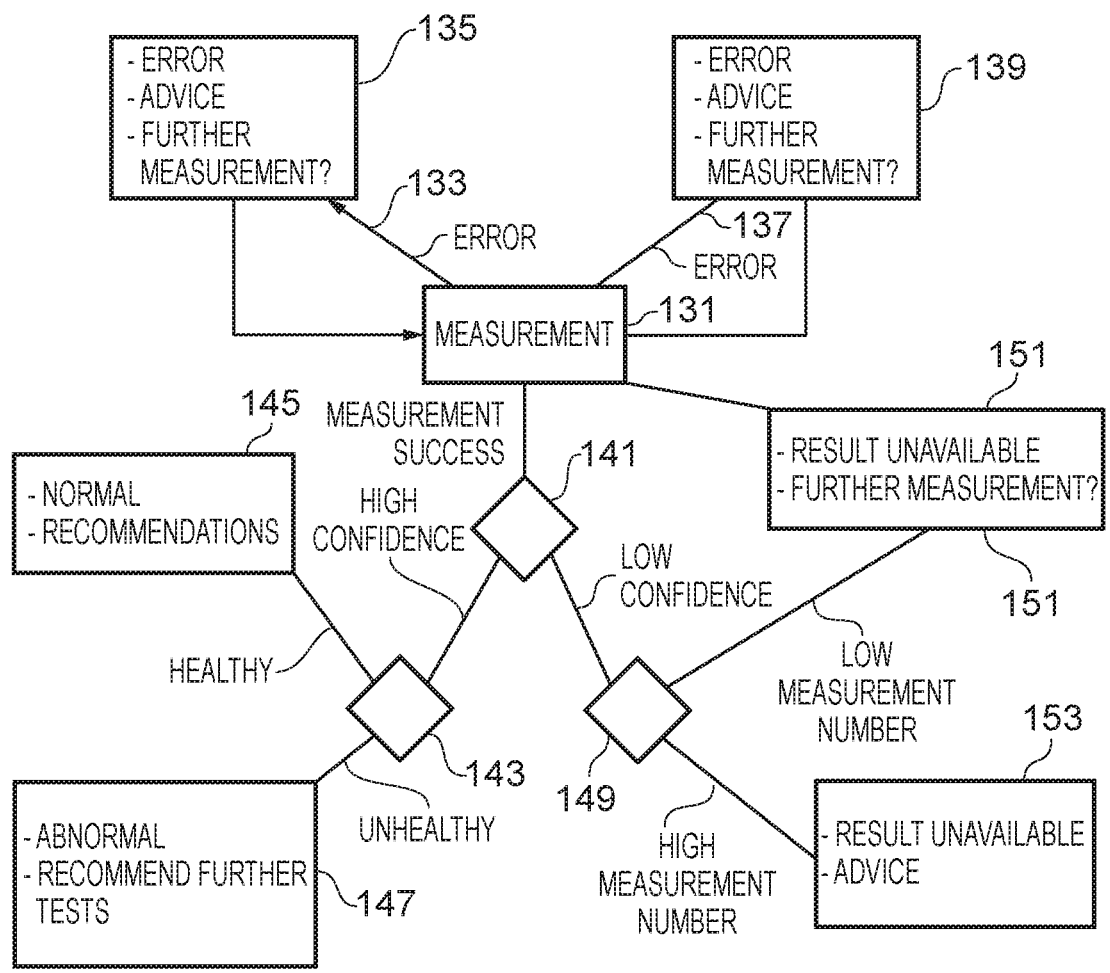
FIG. 13 illustrates another method.

FIG. 13 illustrates a method of using the wearable device 21. The subject 31 may be wearing the wearable device 21 as shown in FIG. 3. The subject 31 may be operating the wearable device 21 independently, that is, the subject 31 can attach the wearable device 21 to their body and initiate the measurements without any assistance from a physician or medical technician.

The method comprises, at block 131, making a measurement. In order to make the measurement the controlling circuitry 3 may control the audio sensors 23 and the further sensors 25 to detect the heartbeat signals of the subject 31. The audio signals and the further signals may then be provided to the controlling circuitry to enable the audio signals and the further signals to be analyzed.

The recorded audio signals is named 'phonocardiogram'.

At block 133 it may be determined that there is an error in the further signal obtained by the further sensor 25. For instance, it may be determined that the further signal has a quality level below a given threshold.

If there is an error in the further signal then, at block 135, the user interface 29 may be controlled to provide feedback to the subject 31. In some examples the feedback could comprise information indicating that an error has occurred. This information may include the type of error that has occurred.

In some examples the feedback could comprise information advising the subject 31 how to operate the wearable device 21 so as to reduce the risk of an error. For example, it may provide an indication of how to reposition the wearable device 21 or how the subject 31 should be positioning their body.

The feedback may also comprise an option to enable the subject 31 to control the wearable device 21 to make another measurement. If the subject 31 selects making another measurement then, the method returns to block 131.

At block 137 it may be determined that there is an error in the audio signal obtained by the audio sensor 23. For instance, it may be determined that the audio signal has a quality level below a given threshold.

If there is an error in the audio signal then, at block 139, the user interface 29 may be controlled to provide feedback to the subject 31. In some examples the feedback could comprise information indicating that an error has occurred. This information may include the type of error that has occurred. For example, it may indicate the cause of the error as the subject 31 speaking or other people talking or other noises in the environment around the subject 31.

The feedback provided at block 139 could comprise information advising the subject 31 how to operate the wearable device 21 so as to reduce the risk of an error. The feedback could be specific to the type of error that has been detected. For example, if it has been detected that the subject 31 has been talking during the measurement period the advice may be that subject 31 should not talk for the duration of the measurement.

The feedback may also comprise an option to enable the subject 31 to control the wearable device 21 to make another measurement. If the subject selects making another measurement then, the method returns to block 131.

If the measurement is successfully made then, at block 141 it is determined whether or not there is a high confidence in the measurement or a low confidence. The level of confidence in the measurement may be determined by the level of confidence in which the audio signals can be classified.

If there is a high confidence in the classification level then at block 143 the audio signal is classified and the user interface 29 is controlled to provide an output indicative of the classification.

If the audio signal has been classified as a healthy audio signal then, at block 145, the user interface 29 is controlled to provide an indication to the subject 31 that their heartbeat has been classified as normal. In some examples the feedback may also provide further information, for example it may provide recommendations to the subject 31 as to when to take another measurement or of what behaviors they should be following.

If the audio signal has been classified as an unhealthy audio signal then, at block 147, the user interface 29 is controlled to provide an indication to the subject 31 that their heartbeat has been classified as abnormal. In some examples the feedback may also provide further information, for example it may provide recommendations to the subject 31 that they should go to see a physician or other medical professional or suggest further tests that should be carried out in order to enable a diagnosis to be made.

If there is a low confidence in the classification level then at block 149 it is determined how many measurements have been made. It may be determined that the number of measurements that have been made are above or below a threshold level. If the number of measurements is below the threshold level then the number of measurements may be determined to be low whereas if the number or measurements is above the threshold level then the number of measurements may be determined to be high.

If the number of measurements is determined to be low then, at block 151 the user interface 29 is controlled to provide feedback to the subject 31 indicating that the result is not available. The feedback provided may also comprise an option to enable another measurement. In some examples, the another measurement could be scheduled for a later time. For example, the another measurement could be scheduled to be taken several hours later.

If the number of measurements is determined to be high then, at block 153 the user interface 29 is controlled to provide feedback to the subject 31 indicating that the result is not available. The feedback provided may also comprise advice for the subject, for example, it may comprise advice relating to the use and/or positioning of the wearable device 21. In some examples the advice could be to go to see a physician or other medical professional.

Voice activity detection is based on the analysis of the frequency content of the stethoscope signal. Two features, namely ZCR (zero-crossing rate) and spectral flatness are extracted on small segments of the signal. If both are greater than given thresholds during a long enough duration, this denotes that voice is detected.

ZCR is the rate of sign-changes along a signal time chart. It is used in speech recognition and it can be sometimes used as a pitch detector in tonal signals. A voiced signal will have a high ZCR during long durations whereas an unvoiced signal will have a low ZCR almost everywhere.

Spectral Flatness (also known as Wiener entropy) measures how tone-like versus how noisy a signal is. Maximum spectral flatness will be obtained for white noise (which has a flat frequency spectrum). It is calculated as the geometric mean of the audio spectrogram of the signal (for example from a simplified or fast Fourier transform).

So both features, namely ZCR and spectral flatness, exploit the fact that voice have a fundamental frequency (ZCR looks for the main pitch, spectral flatness also looks for the harmonics).

The target is to distinguish between voiced signal and sounds from valvular heart diseases. The proposed method uses:
  choosing with machine learning the threshold above which voice is detected
  exploiting the duration differences between voice segments which are longer than sounds of heart with valvular heart disease.

High-low confidences (block 141 FIG. 13) are given by the output of the classifier (block 56 FIG. 5) which, in practice, predicts a continuous value between 0 (healthy) and 1 (not healthy). Values close to 0 and close to 1 are considered as 'high confidence'. Values close to 0.5 are low confidence. These values are therefore based mostly on the analysis of the frequency content of segmented heart beats.

According to another the output of the classifier (block 56), another classifier index predicts a continuous value between 0 (healthy) and 1 (aortic stenosis), and another classifier index predicts a continuous value between 0 (healthy) and 1 (mitral regurgitation).

Wavelet denoising (block 54) removes a certain quantity of noise. If the amount of noise is greater than a given threshold, the signal at stake can be rejected as it is it is too noisy to enable a reliable detection.

The blocks illustrated in FIGS. 4, 5, 11 and 13 may represent steps in a method and/or sections of code in the computer program 9. The illustration of a particular order to the blocks does not necessarily imply that there is a required or preferred order for the blocks and the order and arrangement of the block may be varied. Furthermore, it may be possible for some blocks to be omitted. For example, in the described methods the audio signal and the further signal could be obtain in any order and may be obtained simultaneously.

The example methods of FIGS. 4, 5, 11 and 13 may be performed by an apparatus 1 which may be within a wearable device 21. In some examples all of the blocks of the methods may be carried out by the apparatus 1 within the wearable device 21. This may enable the detection of the heartbeat signals and the analysis of the audio signals to be performed by a single device.

In this description the term coupled means operationally coupled. Any number of components may exist between coupled components including no intervening elements.

Examples of the disclosure therefore provide apparatus, methods and computer programs that enable analysis of heartbeat signals. In examples of the disclosure both the sensors 23, 25 and the controlling circuitry 3 which performs the analysis can be provided in the same wearable device 21. This provides for one single device 21 that can perform dual functions. There is no requirement for an additional processing device or other peripheral device.

In examples of the disclosure the use of the further signal to identify the individual heartbeats in an audio signal enables a low quality audio signal to be used. This means that a reliable level of classification can be made for the audio signals even when the audio signals may be of poor quality. This means that the audio sensor 23 does not need to be positioned in an optimal position. Normally a physician would place a stethoscope over a subject's heart 35 in order to hear the sound of the heartbeat. However this requires skill in the positioning of the stethoscope. The examples of the disclosure do not require the same level of precision for the positioning of the audio sensors 23 so the operation of the wearable device 21 can be performed by an unskilled person, who could be the subject 31.

As the embodiments of the disclosure can use low quality audio signals the audio sensor can be positioned underneath the subject's arm 33 instead of on the chest of the subject 31. This enables the audio sensor 23 to be provided within a cuff 37 which can then be wrapped around the upper arm of the subject 31. This therefore provides for a convenient wearable device 21 which can easily be attached to the arm of the subject 31. The wearable device 21 could also be used to obtain other measurements such as the blood pressure of the subject 31.

In examples of the disclosure the shape of the heartbeats within the signal are identified. This provides more detailed information than a signal which just comprises the pulse of the subject and may enable more detailed and more accurate classifications of the heartbeat signals.

According to another aspect of the disclosure, the apparatus 1 comprises a wireless interface to send data to a remote device such as a smartphone or computer (not illustrated at figures). Wireless protocol can be Bluetooth, WIFI, wireless local area network (wireless LAN) or any other suitable protocol.

The remote device comprises an application and/or a client application that forms a enhanced user interface.

The apparatus 1 is configured to forward the collected data (recorded phonocardiogram and associated data) to the application of the remote device.

The remote device comprises a loudspeaker. The remote device is configured to replay the recorded phonocardiogram on demand. Upon request and or authorization from the user, the remote device is configured to forward the collected data (phonocardiogram and associated data) to a medical professional (physician, caretaker, nurse, . . . ). Said medical professional can confirm or not the preliminary diagnostic issued by the apparatus.

In the application, there may be provided a personal history of previously recorded phonocardiograms.

The term "comprise" is used in this document with an inclusive not an exclusive meaning. That is any reference to X comprising Y indicates that X may comprise only one Y or may comprise more than one Y. If it is intended to use "comprise" with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term "example" or "for example" or "may" in the text denotes, whether explicitly stated or not, that such features or functions are present in at least the described example, whether described as an example or not, and that they can be, but are not necessarily, present in some of or all other examples. Thus "example", "for example" or "may" refers to a particular instance in a class of examples. A property of the instance can be a property of only that instance or a property of the class or a property of a sub-class of the class that includes some but not all of the instances in the class. It is therefore implicitly disclosed that a feature described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed. For instance, in the examples described above the sensors 23, 25 and the apparatus 1 are all integrated within a single device. In other examples one or more of these components could be provided within a different device. For instance, controlling circuitry 3 could be provided within a different device, such as a mobile device. The mobile device could then be used to perform the processing of the heartbeat signals.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. An apparatus comprising an audio sensing means, a further sensing means, attachment means for attaching the apparatus to a subject, wherein the audio sensing means is positioned within the apparatus so that when the apparatus is attached to the subject the audio sensing means is positioned adjacent to the subject's torso underneath the subject's arm in order to detect sound signals generated by the subject's heart, the apparatus further comprising a processing circuitry and a memory circuitry including a computer program code, the memory circuitry and the computer program code arranged to, with the processing circuitry, cause the apparatus to:

obtain an audio signal from the audio sensing means wherein the audio signal comprises a heartbeat of the subject;

obtain a further signal from the further sensing means wherein the further signal also comprises the heartbeat of the subject;

use the further signal to identify individual heart beats in the audio signal; and analyse the individual heartbeats of the audio signal to enable the audio signal to be classified.

2. The apparatus as claimed in claim 1 wherein the attachment means comprises a cuff which is arranged to fit around the subject's arm.

3. The apparatus as claimed in claim 1 wherein the further sensing means comprises means for sensing a bioelectric signal.

4. The apparatus as claimed in claim 3 wherein the bioelectric signal comprises an electrocardiogram signal.

5. The apparatus as claimed in claim 1 wherein the memory circuitry and the computer program code are configured to, with the processing circuitry, cause the apparatus to identify R peaks in the further signal to enable individual heartbeats in the audio signal to be identified.

6. The apparatus as claimed in claim 1 wherein the memory circuitry and the computer program code are configured to, with the processing circuitry, cause the apparatus to divide the individual heartbeats of the audio signal into segments corresponding to different portions of the heartbeat.

7. The apparatus as claimed in claim 1 wherein the memory circuitry and the computer program code are configured to, with the processing circuitry, cause the apparatus to use wavelets to remove noise from the audio signal.

8. The apparatus as claimed in claim 1 wherein the memory circuitry and the computer program code are configured to, with the processing circuitry, cause the apparatus to extract features from within an individual heartbeat of the audio signal and use the extracted features to classify the audio signal.

9. The apparatus as claimed in claim 1, further comprising a user interface enabling a user to interact with the apparatus, and enabling the apparatus to provide a feedback to the user.

10. The apparatus as claimed in claim 9, wherein the user interface comprises a display arranged to output information for the user.

11. The apparatus as claimed in claim 9, wherein the user interface comprises a loudspeaker arranged to output information for the user.

12. A wearable device comprising the apparatus as claimed in claim 1.

13. A method to be carried out with an apparatus by a user, the method comprising:

S1- obtaining an audio signal from an audio sensing means wherein the audio signal comprises a subject's heartbeat;

S2- giving a feedback to the user upon determination that the obtained audio signal has a quality level below a given threshold, and in which case causing step S1 to be repeated;

S3- obtaining a further signal from a further sensing means wherein the further signal also comprises the subject's heartbeat;

S4- giving a feedback to the user upon determination that the obtained further signal has a quality level below a given threshold, and in which case causing step S3 to be repeated;

S5- using the further signal to identify individual heart beats in the audio signal;

S6- analysing the individual heartbeats of the audio signal;

S7- classifying the individual heartbeats; and

S8- providing a result to the user as to whether the heartbeat of the subject is normal or abnormal;

wherein during step S2, when a quality level of the audio signal is determined, the method includes the determination of a speech occurrence, either one from the subject or from other people talking around.

14. The method as claimed in claim 13, further comprising after step S1 a noise removing process using a wavelet signal transform to retain significant signal portions and to remove noise from the audio signal.

15. The method as claimed in claim 13, further comprising after step S3 a noise removing process using a wavelet signal transform to retain significant signal portions and to remove noise from the further signal.

16. The method as claimed in claim 13, wherein the determination of a speech occurrence is made via assessment of zero-crossing rate and spectral flatness on one or more portions of the audio signal.

17. The method as claimed in claim 13, further comprising:

S9- forwarding the recorded audio signal, named a phonocardiogram, from the apparatus to a remote device having a loudspeaker therein, S10- replaying on demand, at the remote device, the phonocardiogram via the loudspeaker.

18. A computer program comprising computer program instructions that, when executed by processing circuitry, carry out the method of claim 13.

* * * * *